(12) United States Patent
Yoo et al.

(10) Patent No.: US 10,582,912 B2
(45) Date of Patent: Mar. 10, 2020

(54) ULTRASOUND DIAGNOSIS APPARATUS AND OPERATING METHOD THEREOF

(71) Applicant: SAMSUNG MEDISON CO., LTD., Hongcheon-gun (KR)

(72) Inventors: Jun-sang Yoo, Hongcheon-gun (KR); Kwang-hee Lee, Hongcheon-gun (KR); Sung-yoon Kim, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 531 days.

(21) Appl. No.: 15/191,866

(22) Filed: Jun. 24, 2016

(65) Prior Publication Data

US 2017/0007209 A1 Jan. 12, 2017

(30) Foreign Application Priority Data

Jul. 10, 2015 (KR) ........................ 10-2015-0098412

(51) Int. Cl.
| | |
|---|---|
| *A61B 8/08* | (2006.01) |
| *A61B 8/00* | (2006.01) |
| *G06T 7/00* | (2017.01) |
| *A61B 8/14* | (2006.01) |
| *A61B 8/06* | (2006.01) |

(52) U.S. Cl.
CPC ................ *A61B 8/523* (2013.01); *A61B 8/14* (2013.01); *A61B 8/463* (2013.01); *A61B 8/466* (2013.01);
(Continued)

(58) Field of Classification Search
CPC ........... A61B 8/14; A61B 8/463; A61B 8/469; A61B 8/523; A61B 8/466; A61B 8/467;
(Continued)

(56) References Cited

U.S. PATENT DOCUMENTS

| | | | |
|---|---|---|---|
| 8,083,678 B2 | 12/2011 | Abuhamad | |
| 2003/0212327 A1* | 11/2003 | Wang | A61B 6/463 600/437 |

(Continued)

FOREIGN PATENT DOCUMENTS

| | | |
|---|---|---|
| JP | 2009-509615 A | 3/2009 |
| JP | 4824321 B2 * | 11/2011 |

(Continued)

OTHER PUBLICATIONS

Communication dated Nov. 18, 2016, issued by the European Patent Office in counterpart European Patent Application No. 16169095.3.
(Continued)

*Primary Examiner* — Amanda Lauritzen Moher
*Assistant Examiner* — Chao Sheng
(74) *Attorney, Agent, or Firm* — Sughrue Mion, PLLC

(57) ABSTRACT

An ultrasound diagnosis apparatus and a method thereof are provided. The ultrasound diagnosis apparatus includes: a data obtainer configured to obtain volume data of an object; a display configured to display a reference cross-section of the object extracted from the volume data; a user input unit configured to receive a user input selecting a reference object included in the displayed reference cross-section; and an image processor configured to normalize the volume data by using location information of the reference object, and to extract a coronal plane of the object based on information of at least one anatomical landmark included in the normalized volume data, and the display is further configured to display the extracted coronal plane.

16 Claims, 18 Drawing Sheets

(52) U.S. Cl.
CPC .............. *A61B 8/467* (2013.01); *A61B 8/483* (2013.01); *A61B 8/486* (2013.01); *A61B 8/488* (2013.01); *G06T 7/0012* (2013.01); *A61B 8/06* (2013.01); *A61B 8/0808* (2013.01); *A61B 8/0866* (2013.01); *A61B 8/0875* (2013.01); *A61B 8/0883* (2013.01); *A61B 8/4405* (2013.01); *A61B 8/4472* (2013.01); *A61B 8/4483* (2013.01); *A61B 8/469* (2013.01); *A61B 8/5292* (2013.01); *A61B 8/565* (2013.01)

(58) Field of Classification Search
CPC ......... A61B 8/483; A61B 8/486; A61B 8/488; A61B 8/06; A61B 8/0866; A61B 8/4405; A61B 8/4472; A61B 8/4483; A61B 8/565; A61B 8/0808; A61B 8/0875; A61B 8/0883; A61B 8/5292; G06T 7/0012
See application file for complete search history.

(56) References Cited

U.S. PATENT DOCUMENTS

| | | |
|---|---|---|
| 2005/0004465 A1 | 1/2005 | Abuhamad |
| 2005/0171430 A1* | 8/2005 | Zhang .................. A61B 8/0825 600/437 |
| 2006/0034513 A1 | 2/2006 | Cai et al. |
| 2006/0058605 A1* | 3/2006 | Deischinger ............ A61B 8/00 600/407 |
| 2008/0249407 A1 | 10/2008 | Hill et al. |
| 2011/0054324 A1 | 3/2011 | Lee |
| 2013/0170720 A1 | 7/2013 | Hu et al. |
| 2014/0024938 A1 | 1/2014 | Ma et al. |
| 2014/0171800 A1 | 6/2014 | Kondou |
| 2014/0328526 A1 | 11/2014 | Wahrenberg |
| 2014/0336504 A1 | 11/2014 | Zhang et al. |
| 2015/0089337 A1 | 3/2015 | Grady et al. |

FOREIGN PATENT DOCUMENTS

| | | |
|---|---|---|
| JP | 2014-217757 A | 11/2014 |
| JP | 2015-057108 A | 3/2015 |
| WO | 2004/093687 A1 | 11/2004 |

OTHER PUBLICATIONS

Communication dated Dec. 4, 2018, issued by the European Patent Office in counterpart European Application No. 16169095.3.

* cited by examiner

ULTRASOUND DIAGNOSIS APPARATUS AND OPERATING METHOD THEREOF

CROSS-REFERENCE TO RELATED APPLICATION

This application claims the benefit of Korean Patent Application No. 10-2015-0098412, filed on Jul. 10, 2015, in the Korean Intellectual Property Office, the disclosure of which is incorporated herein in its entirety by reference.

BACKGROUND

1. Field

The present disclosure relates to ultrasound diagnosis apparatuses and operating methods thereof, and more particularly, to ultrasound diagnosis apparatuses and operating methods thereof which extract and display a standard cross-section of an object.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

A user such as a doctor needs to read an ultrasound image in order to diagnose a state of an examinee. However, according to an ultrasound system of the related art, kinds of cross-sections that may be extracted are limited when a cross-section of an object (for example, a brain of a fetus) is extracted, and thus only a limited state of an examinee may be observed.

Therefore, as the kinds of cross-sections that may be extracted from an object by an ultrasound diagnosis apparatus increase, accurate and fast diagnosis of the examinee may be possible. Also, if a user may directly edit a cross-section extracted from an object by an ultrasound diagnosis apparatus, user convenience may increase.

SUMMARY

Provided are ultrasound diagnosis apparatuses and operating methods thereof which automatically extract and display various standard cross-sections from volume data of an object by minimizing a user input, and allow a user to directly change a location of the extracted standard cross-sections.

Additional aspects will be set forth in part in the description which follows and, in part, will be apparent from the description, or may be learned by practice of the presented embodiments.

According to an aspect of an embodiment, an ultrasound diagnosis apparatus includes: a data obtainer configured to obtain volume data of an object; a display configured to display a reference cross-section of the object extracted from the volume data; a user input unit configured to receive a user input selecting a reference object included in the displayed reference cross-section; and an image processor configured to normalize the volume data by using location information of the reference object, and to extract a coronal plane of the object based on information of at least one anatomical landmark included in the normalized volume data, and the display is further configured to display the extracted coronal plane.

The at least one anatomical landmark may include an object allowing standard cross-sections of the object to be identified.

The image processor may detect the at least one anatomical landmark based on a predetermined reference value inside a prediction region of the normalized volume data, and extract the coronal plane including the detected at least one anatomical landmark, and the information of the at least one anatomical landmark may include information of at least one of a kind, a location, brightness, and a shape of the at least one anatomical landmark.

The at least one anatomical landmark may include at least one of a cavum septum pellucidum (CSP), thalami, a cerebellum, a ventricle, a choroid plexus (CP), sphenoid bone, a caudate nucleus, and an inter-hemispheric fissure (IHF).

The image processor may be further configured to extract at least one of an axial plane and a sagittal plane of the object from the volume data, and the display may be further configured to display at least one of the extracted axial plane and sagittal plane.

The axial plane may include at least one of a trans-ventricular axial plane (TV), a trans-thalamic axial plane (TT) and a trans-cerebellar axial plane (TC), the sagittal plane may include at least one of a mid-sagittal plane (MPS) and a para-sagittal plane (PSP), and the coronal plane may include at least one of a trans-frontal coronal plane (TFc), a trans-caudate coronal plane (TCaudc), a trans-thalamic coronal plane (TTc), and a trans-cerebellar coronal plane (TCc).

The image processor may be further configured to extract an axial plane of the object, the display may be further configured to display the axial plane and a location of the coronal plane inside the axial plane, the user input unit may be further configured to receive a user input that changes the location of the coronal plane, and the image processor may be further configured to extract a coronal plane corresponding to the changed location from the volume data.

The display may be further configured to display the changed location and the coronal plane corresponding to the changed location.

The image processor may be further configured to operate a difference value between a location before the change of location of the coronal plane and a location after the change of location of the coronal plane, and the display may display the coronal plane corresponding to the changed location and the difference value.

The object may include a human body or a brain of a fetus.

According to an aspect of another embodiment, a method of operating an ultrasound diagnosis apparatus includes: obtaining volume data of an object; displaying a reference cross-section of the object extracted from the volume data; receiving a user input selecting a reference object included in the displayed reference cross-section; normalizing the volume data by using location information of the reference object, and extracting a coronal plane of the object based on location information of at least one anatomical landmark included in the normalized volume data; and displaying the extracted coronal plane.

According to an aspect of another embodiment, a non-transitory computer-readable recording medium having recorded thereon a program for performing the method in order to accomplish the above objects is provided.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as ". . . unit", ". . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, embodiments are described with reference to the drawings.

Figure 1:
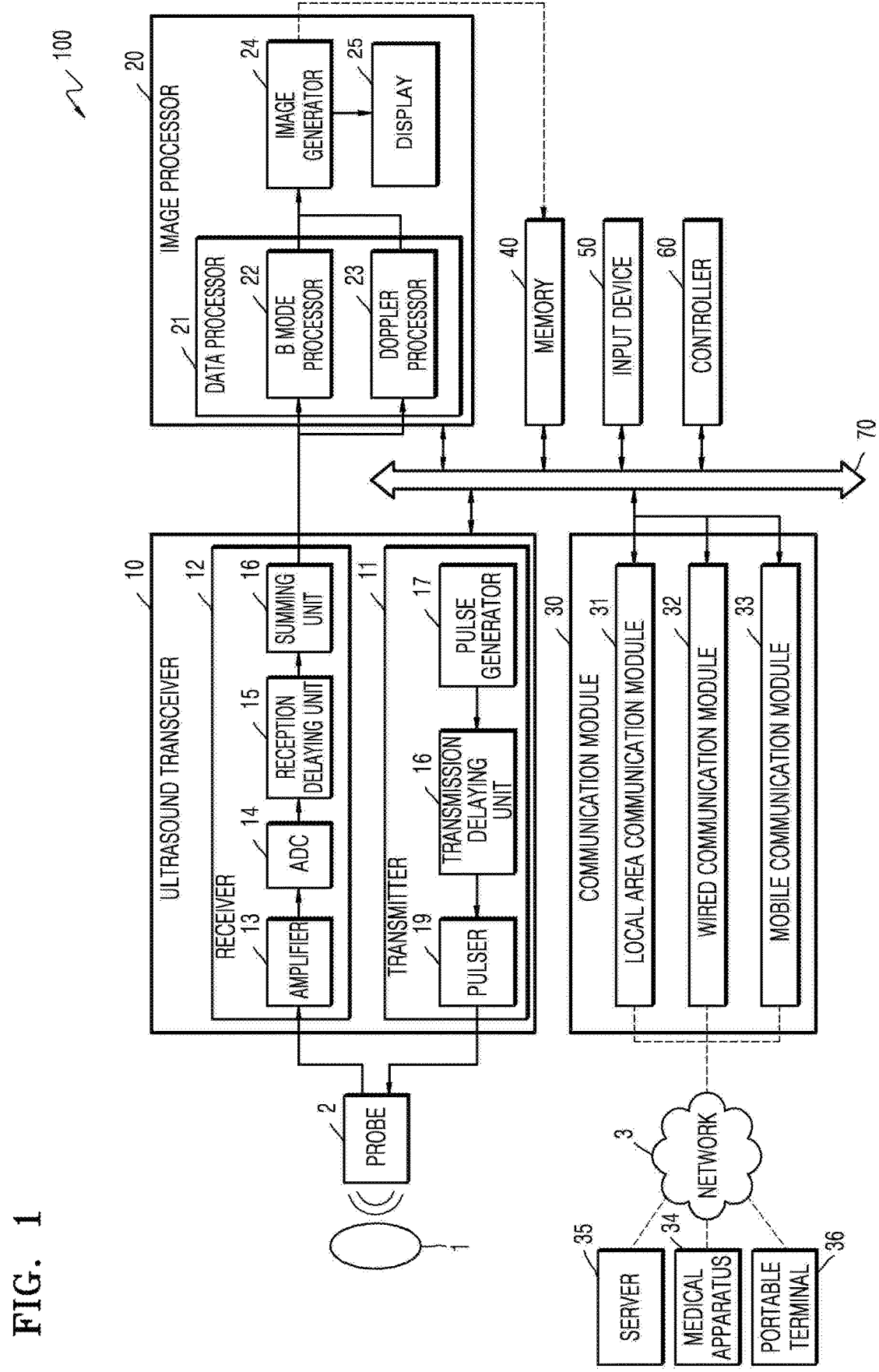
FIG. 1 is a block diagram showing a configuration of an ultrasound diagnosis apparatus according to an embodiment.

FIG. 1 is a block diagram showing a configuration of an ultrasound diagnosis apparatus according to an embodiment. Referring to FIG. 1, the ultrasound diagnosis apparatus 100 may include a probe 2, an ultrasound transceiver 10, an image processor 20, a communication module 30, a display 300, a memory 40, an input device 50, and a controller 60, which may be connected to one another via buses 70.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 2 transmits ultrasound waves to an object 1 in response to a driving signal applied by the ultrasound transceiver 10 and receives echo signals reflected by the object 1. The probe 2 includes a plurality of transducers, and the plurality of transducers oscillate in response to electric signals and generate acoustic energy, that is, ultrasound waves. Furthermore, the probe 2 may be connected to the main body of the ultrasound diagnosis apparatus 100 by wire or wirelessly, and according to embodiments, the ultrasound diagnosis apparatus 100 may include a plurality of probes 2.

A transmitter 11 supplies a driving signal to the probe 2. The transmitter 110 includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 delays the pulses by delay times necessary for determining transmission directionality. The pulses which have been delayed correspond to a plurality of piezoelectric vibrators included in the probe 2, respectively. The pulser 19 applies a driving signal (or a driving pulse) to the probe 2 based on timing corresponding to each of the pulses which have been delayed.

A receiver 12 generates ultrasound data by processing echo signals received from the probe 2. The receiver 120 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion with respect to the amplified echo signals. The reception delaying unit 15 delays digital echo signals output by the ADC 124 by delay times necessary for determining reception directionality, and the summing unit 16 generates ultrasound data by summing the echo signals processed by the reception delaying unit 15. In some embodiments, the receiver 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transceiver 10 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 22 extracts B mode components from ultrasound data and processes the B mode components. An image generator 24 may generate an ultrasound image indicating signal intensities as brightness based on the extracted B mode components 22.

Similarly, a Doppler processor 23 may extract Doppler components from ultrasound data, and the image generator 24 may generate a Doppler image indicating a movement of an object as colors or waveforms based on the extracted Doppler components.

According to an embodiment, the image generator 24 may generate a three-dimensional (3D) ultrasound image via volume-rendering with respect to volume data and may also generate an elasticity image by imaging deformation of the object 1 due to pressure. Furthermore, the image generator 24 may display various pieces of additional information in an ultrasound image by using text and graphics. In addition, the generated ultrasound image may be stored in the memory 40.

A display 25 displays the generated ultrasound image. The display 25 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 25 according to embodiments.

The communication module 30 is connected to a network 3 by wire or wirelessly to communicate with an external device or a server. The communication module 30 may exchange data with a hospital server or another medical apparatus in a hospital, which is connected thereto via a PACS. Furthermore, the communication module 30 may perform data communication according to the digital imaging and communications in medicine (DICOM) standard.

The communication module 30 may transmit or receive data related to diagnosis of an object, e.g., an ultrasound image, ultrasound data, and Doppler data of the object, via the network 3 and may also transmit or receive medical images captured by another medical apparatus, e.g., a computed tomography (CT) apparatus, a magnetic resonance imaging (MRI) apparatus, or an X-ray apparatus. Furthermore, the communication module 30 may receive information about a diagnosis history or medical treatment schedule of a patient from a server and utilizes the received information to diagnose the patient. Furthermore, the communication module 30 may perform data communication not only with a server or a medical apparatus in a hospital, but also with a portable terminal of a medical doctor or patient.

The communication module 30 is connected to the network 3 by wire or wirelessly to exchange data with a server 35, a medical apparatus 34, or a portable terminal 36. The communication module 30 may include one or more components for communication with external devices. For example, the communication module 1300 may include a local area communication module 31, a wired communication module 32, and a mobile communication module 33.

The local area communication module 31 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 32 refers to a module for communication using electric signals or optical signals. Examples of wired communication techniques according to an embodiment may include communication via a twisted pair cable, a coaxial cable, an optical fiber cable, and an Ethernet cable.

The mobile communication module 33 transmits or receives wireless signals to or from at least one selected from a base station, an external terminal, and a server on a mobile communication network. The wireless signals may be voice call signals, video call signals, or various types of data for transmission and reception of text/multimedia messages.

The memory 40 stores various data processed by the ultrasound diagnosis apparatus 100. For example, the memory 40 may store medical data related to diagnosis of an object, such as ultrasound data and an ultrasound image that are input or output, and may also store algorithms or programs which are to be executed in the ultrasound diagnosis apparatus 100.

The memory 40 may be any of various storage media, e.g., a flash memory, a hard disk drive, EEPROM, etc. Furthermore, the ultrasound diagnosis apparatus 100 may utilize web storage or a cloud server that performs the storage function of the memory 40 online.

The input device 50 refers to a means via which a user inputs data for controlling the ultrasound diagnosis apparatus 100. The input device 50 may include hardware components, such as a keypad, a mouse, a touch panel, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 60 may control all operations of the ultrasound diagnosis apparatus 100. In other words, the controller 60 may control operations among the probe 2, the ultrasound transceiver 10, the image processor 20, the communication module 30, the memory 40, and the input device 50 shown in FIG. 1.

All or some of the probe 2, the ultrasound transceiver 10, the image processor 20, the communication module 30, the memory 40, the input device 50, and the controller 60 may be implemented as software modules. However, embodiments of the present invention are not limited thereto, and some of the components stated above may be implemented as hardware modules. Furthermore, at least one selected from the ultrasound transceiver 10, the image processor 20, and the communication module 30 may be included in the controller 60. However, embodiments of the present invention are not limited thereto.

To diagnose a disease by using an ultrasound image, a marker may be set to indicate a predetermined position or set a diagnosis region in an ultrasound image including an object.

In detail, the marker may be set at a portion that is to be observed in detail by the user to diagnose a disease or to check the health of a patient. The inventive concept provides an ultrasound diagnosis apparatus and an ultrasound image display method, which may change and output an ultrasound image to more accurately diagnose an object region in which the marker is set.

Figure 2:
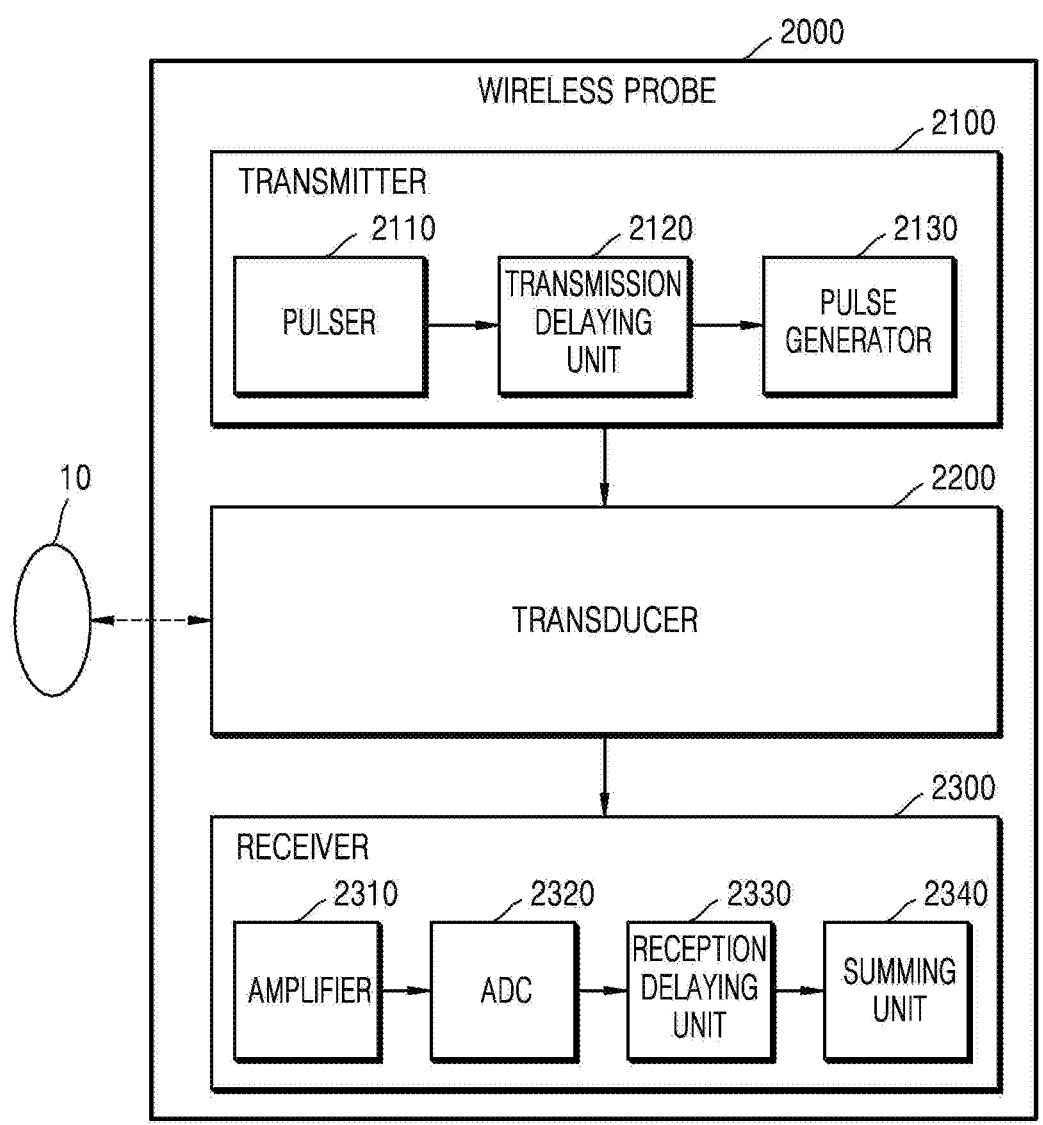
FIG. 2 is a block diagram showing a configuration of a wireless probe 200 according to an embodiment.

FIG. 2 is a block diagram showing a configuration of a wireless probe 200 according to an embodiment. As described above with reference to FIG. 1, the wireless probe 200 may include a plurality of transducers, and, according to embodiments, may include some or all of the components of the ultrasound transceiver 10 shown in FIG. 1.

The wireless probe 200 according to the embodiment shown in FIG. 2 includes a transmitter 210, a transducer 220, and a receiver 230. Since descriptions thereof are given above with reference to FIG. 1, detailed descriptions thereof will be omitted here.

In addition, according to embodiments, the wireless probe 200 may selectively include a reception delaying unit 233 and a summing unit 234.

The wireless probe 200 may transmit ultrasound signals to the object 1, receive echo signals from the object 10, generate ultrasound data, and wirelessly transmit the ultrasound data to the ultrasound diagnosis apparatus 100 shown in FIG. 1.

Hereinafter, an ultrasound diagnosis apparatus and an operating method thereof according to an embodiment are described with reference to FIGS. 3 to 12.

Figure 3:
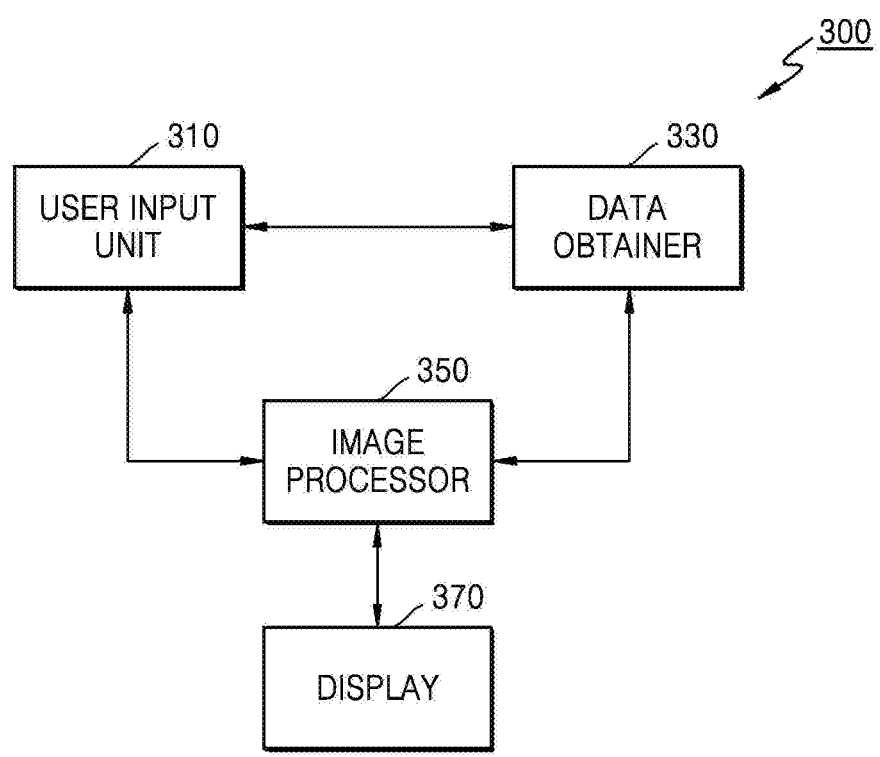
FIG. 3 is a block diagram illustrating a configuration of an ultrasound diagnosis apparatus according to an embodiment.

FIG. 3 is a block diagram illustrating a configuration of an ultrasound diagnosis apparatus 300 according to an embodiment. Referring to FIG. 3, the ultrasound diagnosis apparatus 300 may include a user input unit 310, a data obtainer 330, an image processor 350, and a display 370. The user input unit 310 of FIG. 3 may correspond to an input device 50 of FIG. 1. Also, the data obtainer 330 of FIG. 3 may correspond to the ultrasound transceiver 10 of FIG. 1. Also, the image processor of FIG. 3 may correspond to the image processor 20 of FIG. 1. Also, the display 370 of FIG. 3 may correspond to the display 25 of FIG. 1.

The user input unit 310 is a unit for receiving a user input. The user input unit 310 may include various units that may receive a user input such as a mouse, a keyboard, a track ball, a touchpad, and a touchscreen. A user input by the user input unit 310 may appear as an indicator such as a mouse pointer and a cursor on a view of a standard cross-section.

For example, a user may directly perform an input on a view of a standard cross-section via the user input unit 310. An ultrasound diagnosis apparatus may receive an input for a location of a reference object included in a reference cross-section extracted from volume data of an object. Also, the ultrasound diagnosis apparatus may receive an input for a location of an anatomical landmark included inside volume data. Also, the ultrasound diagnosis apparatus may receive an input for changing geometry of a standard cross-section extracted from an object.

The data obtainer 330 obtains ultrasound data by performing ultrasound capturing on an object 1. Specifically, the data obtainer 330 obtains ultrasound data corresponding to each frame Pi (1≤i≤N) by transmitting an ultrasound signal to an object and receiving an ultrasound signal reflected by the object. Here, the ultrasound signal reflected by the object may be an ultrasound echo signal. Hereinafter, for convenience of description, a case where an object is a fetus is described as an example, but the inventive concept is not limited thereto.

The image processor 350 may obtain a reference cross-section based on ultrasound data obtained from the data obtainer 330. Also, the image processor 350 may normalize ultrasound data based on location information of a reference object included in a reference cross-section, and obtain at least one standard cross-section by using the normalized ultrasound data.

The standard cross-section denotes a cross-section required for diagnosing a state or diseases of an object from among ultrasound images. For example, in the case where an object is a fetus, to observe a growth state corresponding to a number of weeks of a fetus, a user needs to observe a crown rump length (CRL), which is a length from the crown to the rump of the fetus. In the case of intending to observe a CRL, a mid-sagittal plane (MSP), which is a cross-section including the CRL, should be obtained. In the above-described example, a standard cross-section in the case of intending to observe the CRL of the fetus may be an MSP. Here, standard cross-sections may be classified into an axial plane (horizontal plane; transverse plane), a sagittal plane (median plane), and a coronal plane (frontal plane) depending on a direction and a location in which an object is viewed.

For example, in the case of observing a heart via an ultrasound diagnosis apparatus, a standard cross-section may include a four-chamber view, a five chamber view, a three vessel view, RVOT, LVOT, a bicaval view, an aortic arch, a ductral arch, a high short axis view, a low short axis view, etc.

For example, in the case of observing a brain via an ultrasound diagnosis apparatus, a standard cross-section may include a mid-sagittal plane (MSP), a trans-ventricular axial plane (TV), a trans-thalamic axial plane (TT), a trans-cerebellar axial plane (TC), etc. Also, a cross-section that may be observed at an ultrasound diagnosis apparatus according to an embodiment may include a para-sagittal plane (PSP), and the coronal plane may include at least one of a trans-frontal coronal plane (TFc), a trans-caudate coronal plane (TCaudc), a trans-thalamic coronal plane (TTc), and a trans-cerebellar coronal plane (TCc).

In the case of an entire fetus, an object that may be observed inside a standard cross-section may include a CRL, a nuchal translucency, etc. Also, in the case of observing a brain of a fetus, an object that may be observed inside a standard cross-section may include a frontal horn, a cavum septi pellucidi (CSP), an atrium, a choroid plexus, a thalami, a hyppocampal gyrus, a cerebellum, a cisterna magna, a corpus callosum, a lateral ventricle, an inter-hemispheric fissure (IHF), occipital horns, etc. Also, in the case of observing a bone, an object that may be observed inside a standard cross-section may include a femur, a tibia, a fibula, a ulna, a radius, a humerus, etc. According to an ultrasound diagnosis apparatus according to an embodiment, the observation object may be obtained by extracting the above-described standard cross-sections.

A method of extracting a standard cross-section may include at least one of training, a Harr pattern, and Sobel detection. The training is a method of finding out a cross-section by repeating a process of detecting a pattern. The Harr pattern is a method of finding out a cross-section by using a Harr feature having high similarity with a specific pattern from among a plurality of Harr features. The Sobel detection is a method of finding out a cross-section by detecting an outline on an image.

An ultrasound diagnosis apparatus according to an embodiment may normalize volume data of an object before extracting a standard cross-section. This is because an error may occur in the case where a size or a direction of volume data obtained from the data obtainer 330 deviates from reference data set suitable for extracting the standard cross-section. Here, the reference data may include data of a graphic guide. An ultrasound diagnosis apparatus according to an embodiment may extract an arbitrary reference cross-section from volume data. The ultrasound diagnosis apparatus may extract an axial plane (that is, a TV, a TT, and a TC) of an object as an arbitrary reference cross-section, but is not limited thereto. The ultrasound diagnosis apparatus according to an embodiment may receive a user input selecting a reference object inside a reference cross-section, and normalize volume data based on location information of the selected reference object.

More specifically, the image processor 350 according to an embodiment may normalize volume data according to location information of a reference object selected by a user. The reference object may be defined as a reference region inside a reference cross-section for normalizing entire volume data. The ultrasound diagnosis apparatus may standardize or normalize a direction, a size, or a location of volume data by using at least one reference object as a seed. For example, the reference object may include an IHF, a CSP, etc. The image processor 350 according to an embodiment may allow volume data to match a graphic guide based on location information of a reference object selected by a user. In this case, the image processor 350 according to an embodiment may normalize volume data by comparing data for an outline of a brain, an outline of a cerebrum, and an entire outline of a brain detected by an outline detector (not shown) with the location information of the reference object. For example, the outline detector (not shown) may determine an outline of a brain based on a location of at least one reference object or a distance and an angle between reference objects, and the image processor 350 may compare the determined outline of the brain with reference data (for example, a guide line of a graphic guide). In the case where the determined outline of the brain does not coincide with a guide line of the graphic guide, the image processor 350 may adjust (that is, enlarge or reduce) a size of volume data or correct a direction of the volume data with respect to the relevant non-coincidence portion.

The anatomical landmark (an object included in a brain of a fetus) is an object used as a reference in order to extract a standard cross-section. Information of the anatomical landmark may include information representing a kind, a location, a direction, brightness, etc. of an object. The image processor 350 may automatically obtain information of the anatomical landmark from the normalized volume data of the object. For example, the image processor 350 may perform an image process such as an outline improvement filter on volume data, and obtain location information, brightness information, direction information, etc. of an object included in an object. Also, the image processor 350 may automatically extract a standard cross-section including anatomical landmarks based on information of the one or more anatomical landmarks. For example, the image processor 350 may extract a cross-section connecting one or more anatomical landmarks as a standard cross-section. An anatomical landmark used for extracting a standard cross-section may include a cavum septum pellucidum (CSP), thalami, a cerebellum, a ventricle, a choroid plexus (CP), a sphenoidal bone, a caudate nucleus, an inter-hemispheric fissure (IHF), etc.

Additionally, the image processor 350 may extract a new standard cross-section based on a received user input. For example, a user may desire to change geometry of an extracted standard cross-section when needed. The image processor 350 according to an embodiment may display an edit screen for changing a location of an extracted standard cross-section via the display 370. The edit screen may include an arbitrary reference cross-section including an indicator for representing a relative location of the extracted standard cross-section. The indicator may be displayed on a TV, a TT, or a TC to represent a relative location of a standard cross-section whose location is to be changed. For example, in the case where a standard cross-section automatically extracted by the image processor 350 is inaccurate or not suitable for diagnosing or observing an object, a user may change a location of the indicator displayed on an arbitrary reference cross-section via the user input unit 310. The image processor 350 may extract a new standard cross-section corresponding to a location of the changed indicator and display the extracted cross-section via the display 370. Here, the user input may be input in real-time, and the new standard cross-section may be extracted in real-time according to the user input.

The display 370 may display a reference cross-section of an object extracted from volume data. Also, the display 370 may display at least one standard cross-section extracted by the image processor 350. Also, the display 370 may display an edit screen for changing a location of the extracted standard cross-section.

Figure 4A:
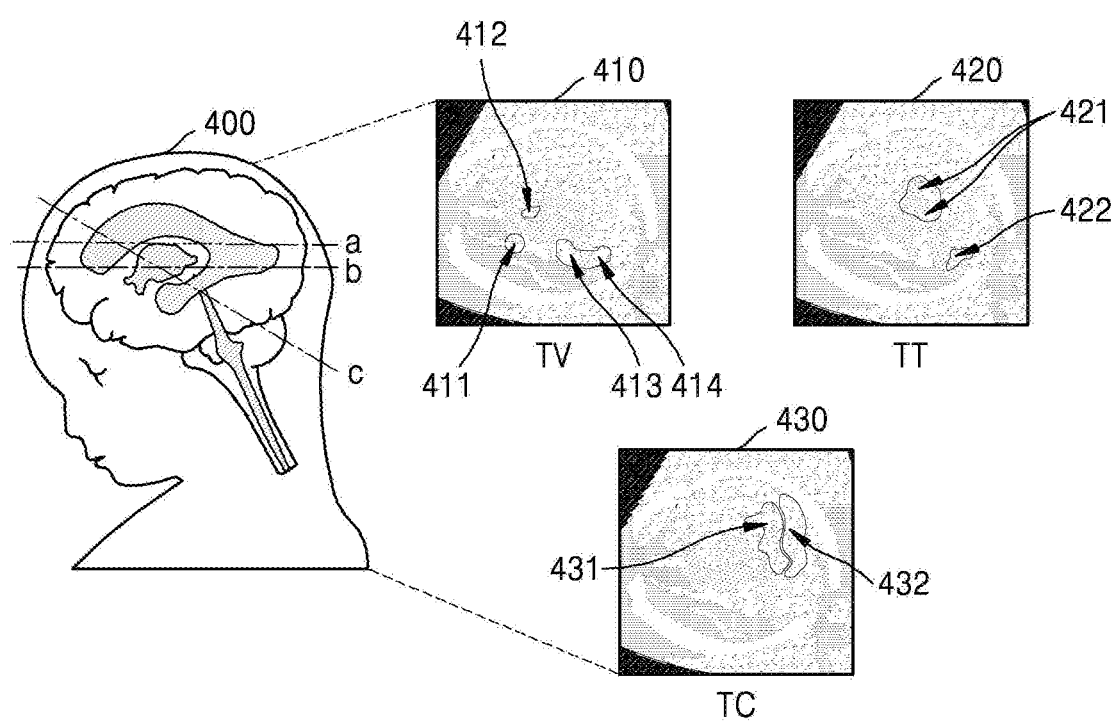
FIG. 4A is a diagram illustrating axial planes of an object according to an embodiment.
Figure 4B:
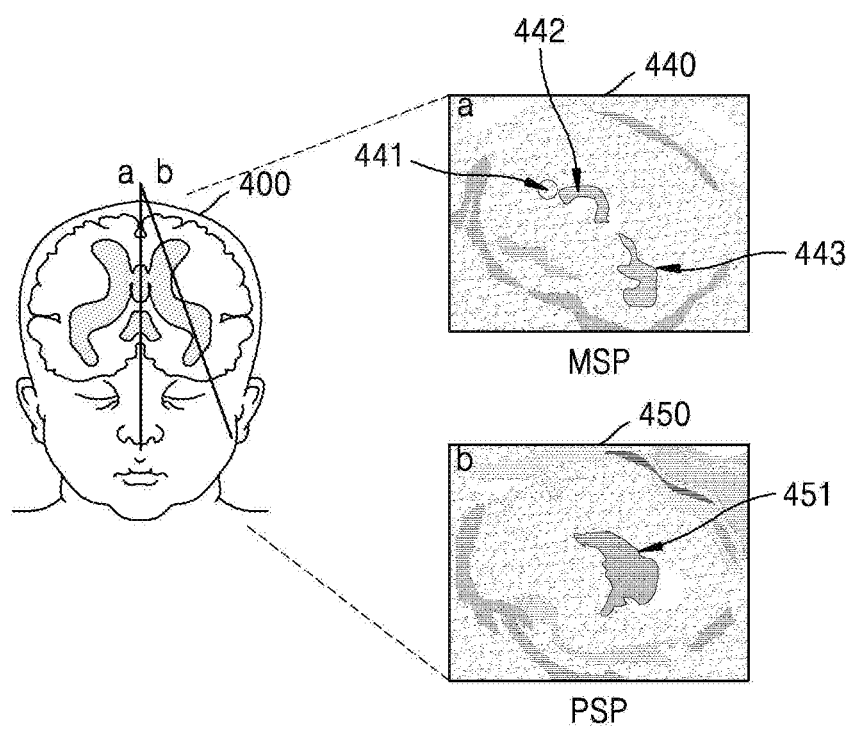
FIG. 4B is a diagram illustrating sagittal planes of an object according to an embodiment.
Figure 4C:
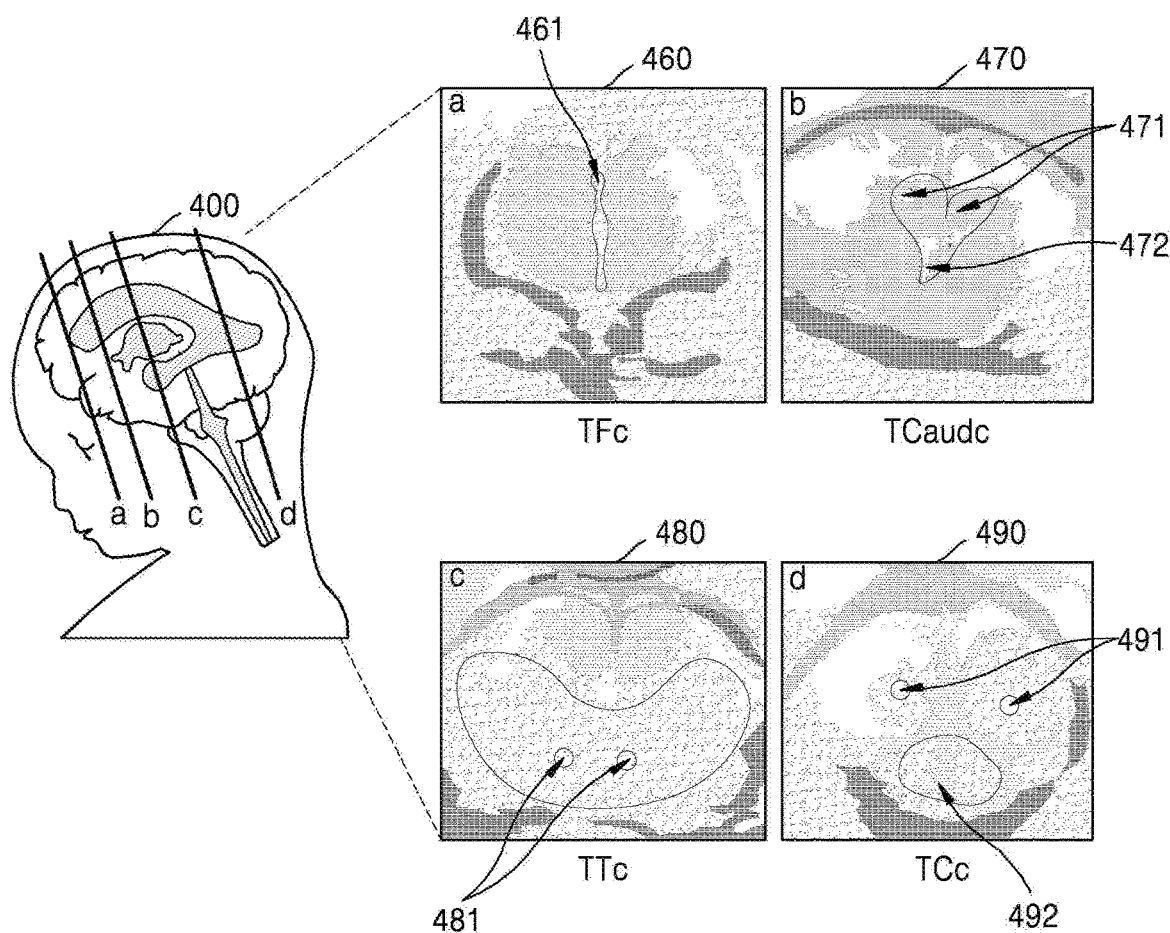
FIG. 4C is a diagram illustrating coronal planes of an object according to an embodiment.

FIG. 4 is a diagram illustrating kinds of a standard cross-section of an object according to an embodiment. Specifically, FIG. 4A is a diagram illustrating axial planes of an object according to an embodiment, FIG. 4B is a diagram illustrating sagittal planes of an object according to an embodiment, and FIG. 4C is a diagram illustrating coronal planes of an object according to an embodiment.

Referring to FIG. 4A, an ultrasound diagnosis apparatus according to an embodiment may obtain a trans-ventricular axial plane (TV) 410, which is a standard cross-section, by observing an object 400 via an axial plane (or axial cross-section) including a line "a". Also, the ultrasound diagnosis apparatus according to an embodiment may obtain a trans-thalamic axial plane (TT) 420, which is a standard cross-section, by observing the object 400 via an axial plane including a line "b". Also, the ultrasound diagnosis apparatus according to an embodiment may obtain a trans-cerebellar axial plane (TC) 430, which is a standard cross-section, by observing the object 400 via an axial plane including a line "c". The TV 410 may include a frontal horn 411, a cavum septi pellucidi 412, an atrium 413, and a choroid plexus 414. The TT 420 may include thalami 421 and a hyppocampal gyrus 422. The TC 430 may include a cerebellum 431 and a cisterna magna 432.

Also, referring to FIG. 4B, the ultrasound diagnosis apparatus according to an embodiment may obtain a mid-sagittal plane (MSP) 440, which is a standard cross-section, by observing the object 400 via a sagittal plane including a line "a". Also, the ultrasound diagnosis apparatus according to an embodiment may obtain a para-sagittal plane (PSP) 450, which is a standard cross-section, by observing the object 400 via a sagittal plane including a line "b". The MSP 440 may include a corpus callosum 441, a cavum septi pellucidi 442, and a cerebellum 443. The PSP 450 may include a lateral ventricle 451. Here, the MSP 440 may be a standard cross-section serving as a basis of extracting the TV 410, the TT 420, and the TC 430.

Also, referring to FIG. 4C, the ultrasound diagnosis apparatus according to an embodiment may obtain a trans-frontal coronal plane (TFc) 460, which is a standard cross-section, by observing the object 400 via a coronal plane including a line "a". Also, the ultrasound diagnosis apparatus according to an embodiment may obtain a trans-caudate coronal plane (TCaudc) 470, which is a standard cross-section, by observing the object 400 via a coronal plane including a line "b". Also, the ultrasound diagnosis apparatus according to an embodiment may obtain a trans-thalamic coronal plane (TTc) 480, which is a standard cross-section, by observing the object 400 via a coronal plane including a line "c". Also, the ultrasound diagnosis apparatus according to an embodiment may obtain a trans-cerebellar coronal plane (TCc) 490, which is a standard cross-section, by observing the object 400 via a coronal plane including a line "d". The TFc 460 may include an inter-hemispheric fissure 461. The Tcaudc 470 may include frontal horns 471 and a cavum septum pellucidum 472. The TTc 480 may include thalami 481. The TCc 490 may include occipital horns 591 and a cerebellum 492.

That is, as described above, objects that may be observed by a user may be different for each kind of a standard cross-section.

FIGS. 5A to 5E are diagrams illustrating a process of extracting a standard cross-section (that is, TFc, TCaudc, TTc, TCc, and PSP) of an object based on location information of an anatomical landmark according to an embodiment. The anatomical landmark is an object used as a reference in order to extract a standard cross-section, and information of the anatomical landmark may include information representing a kind, a location, brightness, a direction, etc. of an object.

Figure 5A:
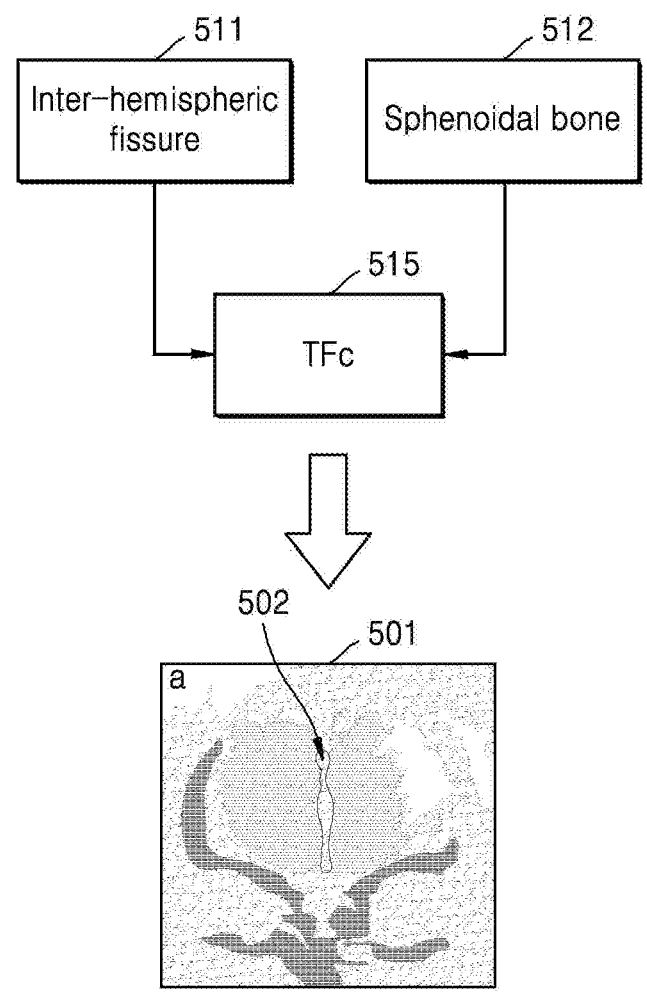
FIGS. 5A to 5E are diagrams illustrating a process of extracting a standard cross-section of an object based on location information of an anatomical landmark according to an embodiment.
Figure 5B:
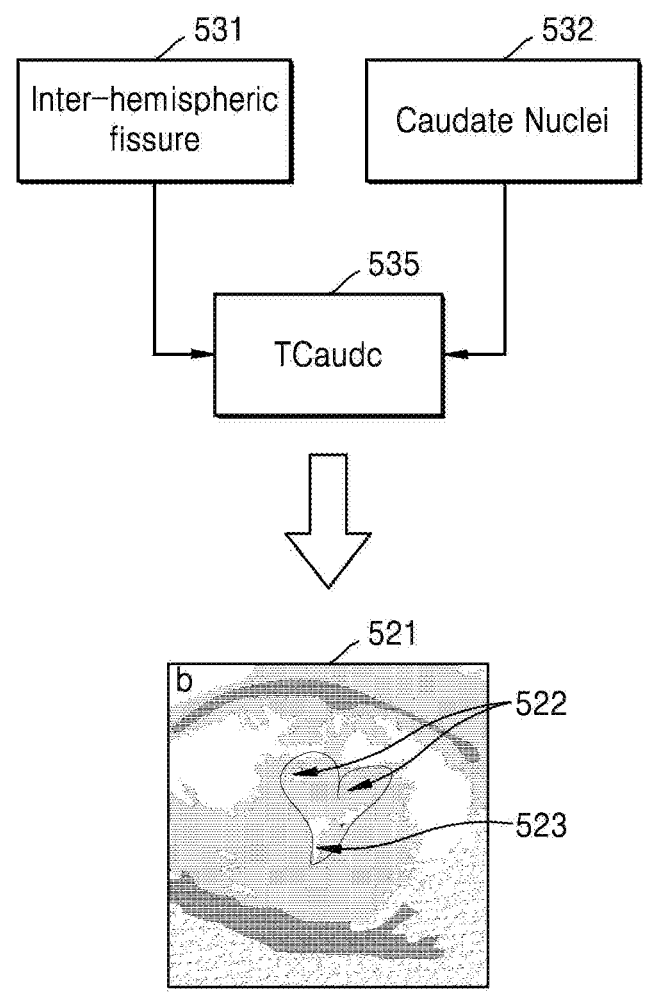
Figure 5C:
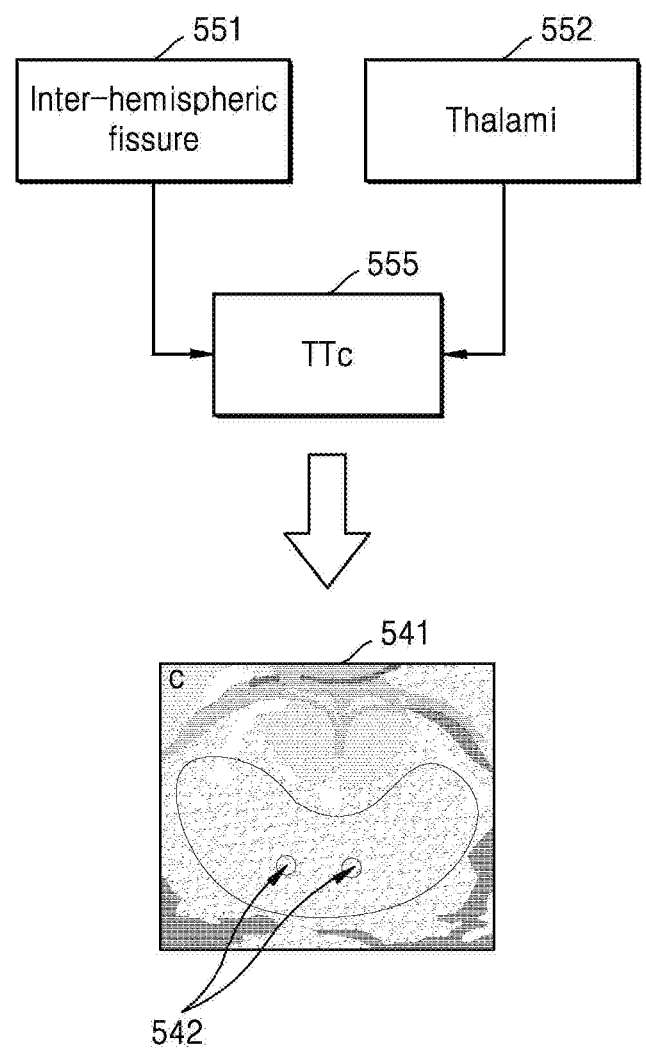
Figure 5D:
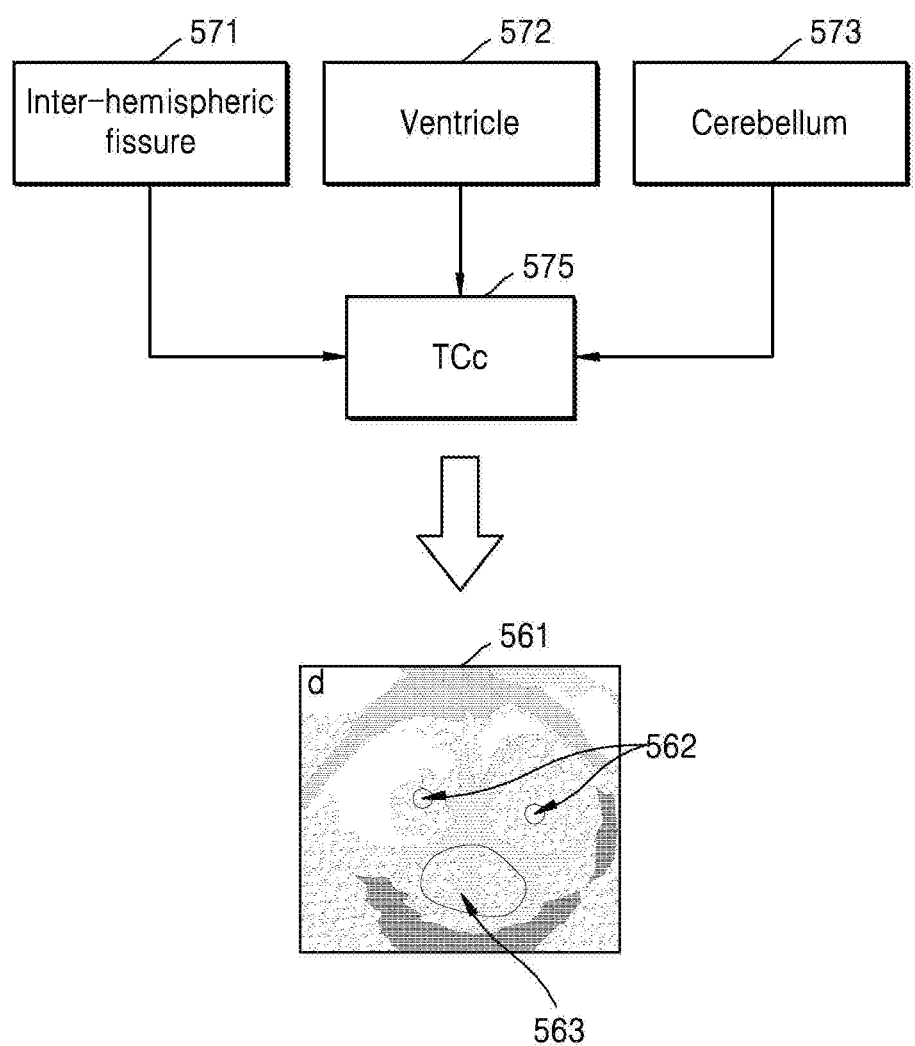
Figure 5E:
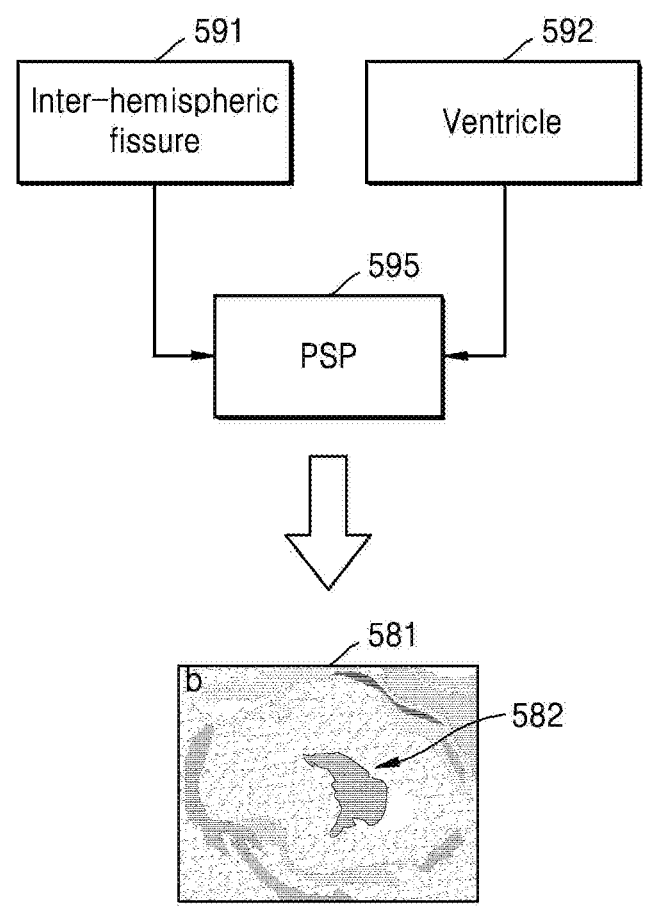

Referring to FIG. 5A, TFc 501 and 515 from among coronal planes may be extracted based on IHF 502 and 511 and a sphenoidal bone 512, which are anatomical landmarks. Also, referring to FIG. 5B, TCaudc 521 and 535 from among coronal planes may be extracted based on an IHF 531 and a caudate nuclei 532, which are anatomical landmarks. The extracted TCaudc 521 may include frontal horns 522 and a CSP 523. Referring to FIG. 5C, TTc 541 and 555 from among coronal planes may be extracted based on an IHF 551 and thalami 542 and 552, which are anatomical landmarks. Also, referring to FIG. 5D, TCc 561 and 575 from among coronal planes may be extracted based on an IHF 571, a ventricle 572, and a cerebellum 563 and 573, which are anatomical landmarks. The extracted TCc 561 may include occipital horns 562 and a cerebellum 563. Also, referring to FIG. 5E, a PSP 581 and 595 from among a sagittal plane may be extracted based on an IHF 591 and a ventricle 592, which are anatomical landmarks. The extracted PSP 581 may include a lateral ventricle 582.

As described above, standard cross-sections may be extracted based on information of an anatomical landmark inside volume data of an object. In this case, the anatomical landmark may be designated via a user input but may be automatically obtained by the image processor 350 of the ultrasound diagnosis apparatus 300. A process of obtaining information of an anatomical landmark at the image processor 350 according to an embodiment is described below with reference to FIG. 6.

Figure 6:
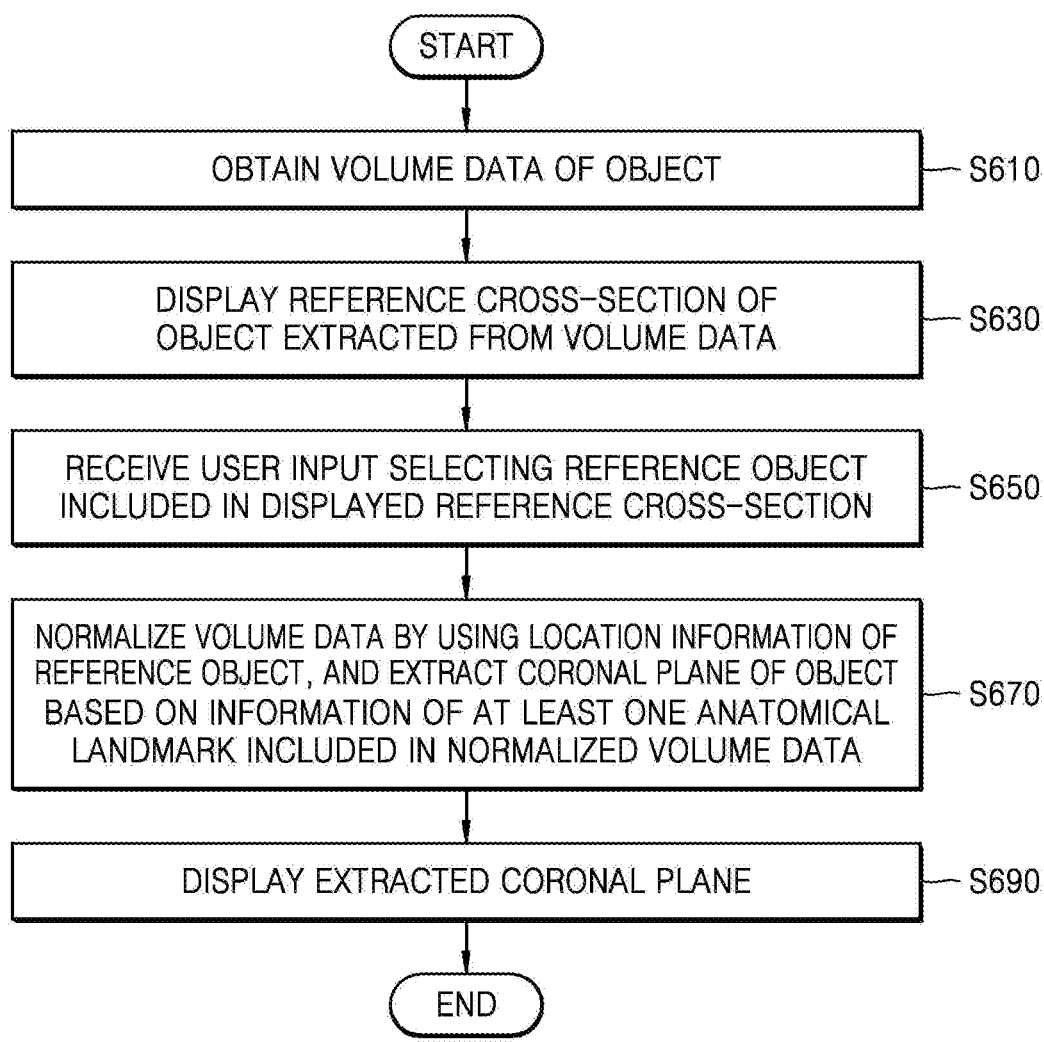
FIG. 6 is a flowchart illustrating a method of operating an ultrasound diagnosis apparatus according to an embodiment.

FIG. 6 is a flowchart illustrating a method of operating an ultrasound diagnosis apparatus according to an embodiment.

The method of operating the ultrasound diagnosis apparatus according to an embodiment may include obtaining volume data of an object (S610), displaying a reference cross-section of the object extracted from the volume data (S620), receiving a user input selecting a reference object included in the displayed reference cross-section (S650), normalizing the volume data by using location information of the reference object and extracting a coronal plane of the object based on information of at least one anatomical landmark included in the normalized volume data (S670), and displaying the extracted coronal plane (S690).

A process of extracting a coronal plane (or a standard cross-section) based on information of an anatomical landmark is described below.

The image processor 350 according to an embodiment may include an anatomical landmark detection controller (not shown) in order to detect a standard cross-section by using an anatomical landmark. The image processor 350 may receive volume data from the data obtainer 330, and may receive volume data from an external device (not shown). The anatomical landmark detection controller (not shown) may generally control a detection operation of an anatomical landmark, basically operate based on an operating system stored in an internal storage device, establish a basic platform environment of the image processor 350, and provide an arbitrary function by executing an application according to a user's selection.

Specifically, the image processor 350 may detect at least one anatomical landmark from volume data received via the anatomical landmark detection controller. Also, the image processor 350 may obtain information of an anatomical landmark including at least one of a location, a kind, brightness, and a shape of the anatomical landmark. Also, the image processor 350 may extract a standard cross-section of an object from volume data by using information of an anatomical landmark. Also, the image processor 350 may control the obtained information of the anatomical landmark to be output to the display 370.

The anatomical landmark detection controller inside the image processor 350 may automatically set a prediction region considered to include an anatomical landmark inside received volume data. Here, the received volume data may be normalized volume data. Also, the prediction region may be manually set by a user and may be set by an external control signal.

Meanwhile, the memory 40 according to an embodiment may store information of a reference value of an anatomical landmark. The memory 40 may include all kinds of storage media such as random access memory (RAM), read only memory (ROM), a hard disk drive (HDD), a flash memory, a CD-ROM, and a DVD.

A reference value for a location, a kind, brightness, and a shape of each anatomical landmark stored in the memory 40 may be set in advance. Also, the image processor 350 may obtain information of an anatomical landmark including at least one of a location, a kind, brightness, and a shape of each anatomical landmark from volume data of an object, and set an average value of the obtained information of the anatomical landmark as a reference value. After that, when a standard cross-section is extracted from the volume data of the object, information of an anatomical landmark included in the extracted standard cross-section is reflected in setting the reference value, so that the reference value of the anatomical landmark stored in the memory 40 may be updated.

The anatomical landmark may be designated as a specific portion existing in common in objects, and may include an object allowing standard cross-sections of an object to be identified. In the case of a brain of a fetus, a cavum septum pellucidum (CSP), thalami, a cerebellum, a ventricle, a choroid plexus (CP), a sphenoidal bone, a caudate nucleus or an inter-hemispheric fissure (IHF) may be designated as anatomical landmarks.

Meanwhile, the image processor 350 may detect at least one anatomical landmark from normalized volume data, and detect other anatomical landmarks based on at least one of distance information or angle information between anatomical landmarks based on the detected anatomical landmarks. For example, since an IHF from among anatomical landmarks may be easily detected relatively, the IHF is detected first from volume data of an object by using the IHF as a reference anatomical landmark, and then a cavum septum pellucidum (CSP), thalami, a cerebellum, a ventricle, a choroid plexus (CP), a sphenoidal bone or a caudate nucleus, which are other anatomical landmarks, may be detected by using distance information or angle information between anatomical landmarks based on a location of the IHF. Therefore, after a reference anatomical landmark whose detection is easy is detected, at least one different anatomical landmark is detected based on the reference anatomical landmark by taking into account distance information or angle information between anatomical landmarks reflecting an anatomical characteristic of an object, so that accuracy of an extracted standard cross-section may increase.

Also, the image processor 350 may extract a standard cross-section of an object from volume data of the object by using information of an anatomical landmark. The image processor 620 may determine whether a detected anatomical landmark is included in a standard cross-section by comparing a reference value of an anatomical landmark stored in the memory 40 with a value related to at least one information of a location, a kind, brightness, and a shape of the detected anatomical landmark. Also, in the case where it is determined that the detected anatomical landmark is included in the standard cross-section, the image processor 350 may extract the cross-section.

The information of the brightness or shape of the anatomical landmark may include at least one information from among a clearness degree, a shape, a size, and brightness of an outline of the anatomical landmark. The image processor 350 may increase accuracy when extracting a standard cross-section by comparing information of a shape or brightness of the anatomical landmark with the reference value.

Also, the display 370 may display information of the detected anatomical landmark, that is, a kind, a shape, brightness, and a location of the anatomical landmark (for example, whether the detected anatomical landmark is a reference anatomical landmark, distance information and angle information between the detected anatomical landmark and the reference anatomical landmark, etc.).

Figure 7:
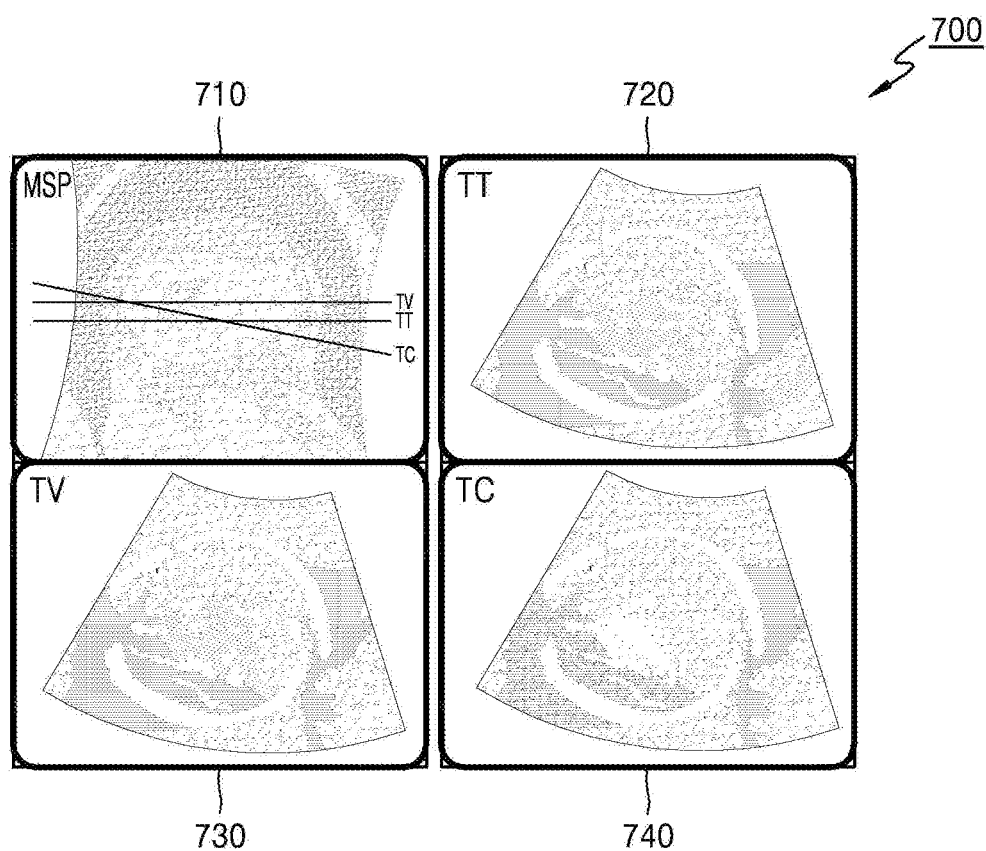
FIG. 7 is a diagram illustrating a display screen of an ultrasound diagnosis apparatus.

FIG. 7 is a diagram illustrating a display screen 700 of an ultrasound diagnosis apparatus.

When ultrasound capturing a brain of a fetus is performed, volume data of a head of the fetus is obtained and an MSP is extracted from the volume data of the head of the fetus. After that, the ultrasound diagnosis apparatus may extract a TT, a TV, and a TC based on the extracted MSP, and display these four standard cross-sections on the screen. As illustrated in FIG. 7, the MSP 710, the TT 720, the TV 730, and the TC 740 may be displayed on one screen, and the locations of the TT 720, the TV 730, and the TC 740 on a region of the MSP 710 may be displayed so that the relative locations of the TT 720, the TV 730, and the TC 740 may be easily recognized.

As described above, a user may observe the four standard cross-sections of an object, that is, the axial planes such as the TV, the TT, and the TC, and the sagittal plane such as the MSP via the ultrasound system. However, there may be a limitation in diagnosing accurately and specifically a state of the object by merely observing the TV, the TT, the TC, and the MSP. If a user intends to extract an arbitrary desired cross-section, an inconvenience of having to input location information of the arbitrary cross-section of the object may occur.

Therefore, when limited kinds of standard cross-sections are extracted and displayed in the ultrasound system, there may be inevitably limitations in diagnosing accurately and specifically even more a state of an object. With regard to accurate observation of an object, since a user may observe various states differently depending on a plane which the user observes, the user needs to utilize additional standard cross-sections (for example, a coronal plane or a PSP).

Figure 8:
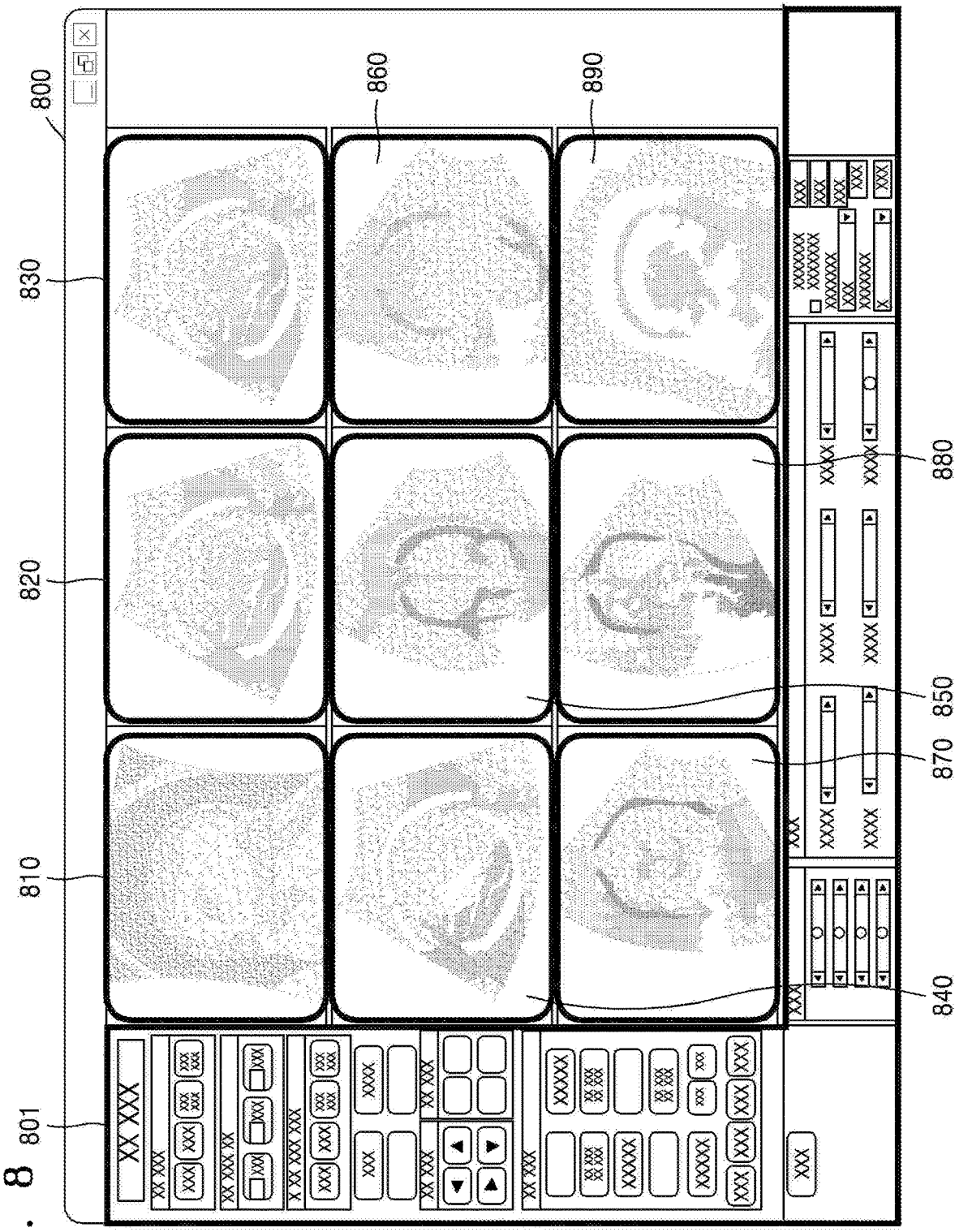
FIG. 8 is a diagram illustrating a display screen of an ultrasound diagnosis apparatus according to an embodiment.

FIG. 8 is a diagram illustrating a display screen 800 of an ultrasound diagnosis apparatus according to an embodiment.

The ultrasound diagnosis apparatus according to an embodiment may display various standard cross-sections. Also, since the ultrasound diagnosis apparatus does not need to directly receive information for extracting an arbitrary cross-section, and standard cross-sections may be automatically extracted and displayed, the screen may be simplified. Various menus 801 may be output on the display screen. The ultrasound diagnosis apparatus may receive a user input via the various menus 801, and means such as a mouse, a keyboard, a track ball, a touchpad, and a touchscreen may be used. A user input via the various menus 801 may appear as an indicator such as a mouse pointer and a cursor on a view of a standard cross-section on the screen.

The display screen 800 of FIG. 8 may display three kinds of axial planes, two kinds of sagittal planes, and four kinds of coronal planes. Specifically, an MSP 810, a TT 820, a TV 830, a TC 840, a TFc 850, a TCaudc 860, a TTc 870, a TCc 880, and a PSP 890 may be displayed. Since various kinds of standard cross-sections may be displayed on the display screen 800, a user may read an ultrasound image more accurately and swiftly. Also, the ultrasound diagnosis apparatus may receive an input selecting one of displayed standard cross-sections from a user. The ultrasound diagnosis apparatus may display detailed information of a standard cross-section selected by a user on the display 370. The detailed information of the selected standard cross-section may include a kind, a location, a size, brightness, etc. of the selected standard cross-section. Also, the ultrasound diagnosis apparatus may display an edit screen for changing geometry of the standard cross-section selected by the user.

Figure 9:
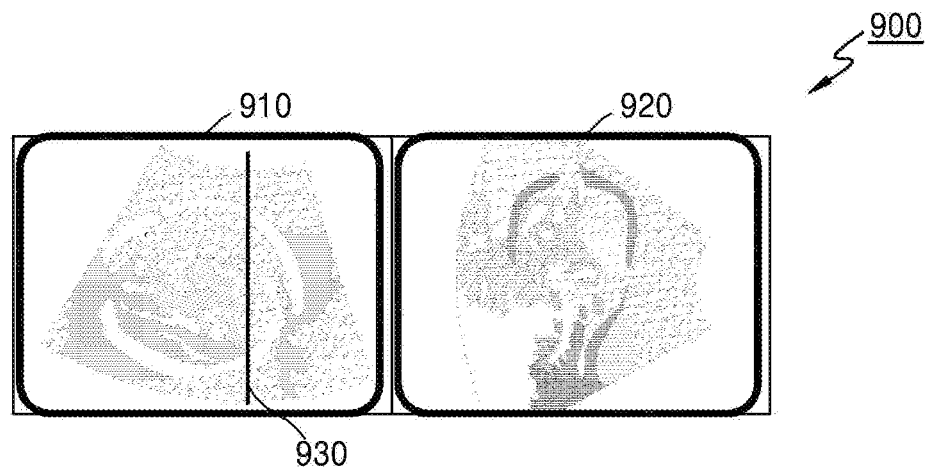
FIG. 9 is a diagram illustrating an edit screen for changing a location of an extracted standard cross-section according to an embodiment.

FIG. 9 is a diagram illustrating an edit screen 900 for changing a location of an extracted standard cross-section according to an embodiment.

In the case of intending to change a location of an already extracted standard cross-section, a user may select a standard cross-section which the user desires to edit. As illustrated in FIG. 9, the edit screen 900 may display a standard cross-section selected by the user, that is, an edit cross-section 920 on the right of the screen, and display an arbitrary reference cross-section 910 for representing a relative location of the standard cross-section selected by the user on the left of the screen. In the detailed description section, for convenience of description, though the edit screen 920 is displayed on the right of the display screen and the reference cross-section 910 is displayed on the left of the display screen, an arrangement configuration of the screen is not limited thereto. Though it is assumed that the reference cross-section 910 is one of the axial planes (that is, the TT, the TV, and the TC), the reference cross-section 910 is not limited thereto. The reference cross-section 910 may be a sagittal plane or a coronal plane. Also, though it is assumed that the standard cross-section selected by the user, that is, the edit cross-section 920 is one of coronal planes such as a TFc, a TCaudc, and a TCc, the edit cross-section 920 is not limited thereto and may be an axial plane or a sagittal plane.

As described above, a standard cross-section automatically obtained by the image processor 350 may be inaccurate or may not be suitable for diagnosing or observing an object. In this case, a user may change a location of the extracted standard cross-section via the user input unit 310. For the user input unit 310, various devices that may receive a user input such as a mouse, a keyboard, a track ball, a touchpad, and a touchscreen may be used. The reference cross-section 910 inside the edit screen 900 may include an indicator 930 for representing a relative location of the edit screen 920.

The ultrasound diagnosis apparatus according to an embodiment may receive an input for changing a location of the indicator 930 on the reference cross-section 910 from a user. The user may change the location of the indicator 930 up/down/left/right by using means such as a mouse, a keyboard, a track ball, a touchpad, and a touchscreen. A change path of the indicator 930 may be displayed as a trace on the edit screen 900. The shape of the indicator 930 may appear as a straight line, a curve, or an arbitrary shape.

The ultrasound diagnosis apparatus according to an embodiment may extract a new standard cross-section (that is, a standard cross-section after the change) corresponding to a location of the changed indicator 930. When the new standard cross-section is extracted, the edit cross-section 920 inside the edit screen 900 may change from the standard cross-section before the change to the standard cross-section after the change. Also, the edit cross-section 920 may be configured to simultaneously represent the standard cross-section before the change and the standard cross-section after the change.

The edit screen 900 for changing a location of an extracted standard cross-section according to an embodiment may display an axial plane as the reference cross-section 910 on the left of the display screen, and display a coronal plane as the edit cross-section on the right of the display screen. In this case, a location of the coronal plane may be displayed as a vertical straight line on the axial plane via the indicator 930.

Also, the ultrasound diagnosis apparatus may operate a difference value between a location of a standard cross-section before the change, and a location of a standard cross-section after the change. The display 370 may display a standard cross-section and a difference value corresponding to the changed location.

As described above, the ultrasound diagnosis apparatus according to an embodiment may obtain a new ultrasound image again based on at least one of an input received from a user and already obtained data. Also, the ultrasound diagnosis apparatus may obtain a user input based on a newly obtained ultrasound image. The user input may be input in real-time, and the new ultrasound image may be obtained in real-time according to the user input.

Figure 10:
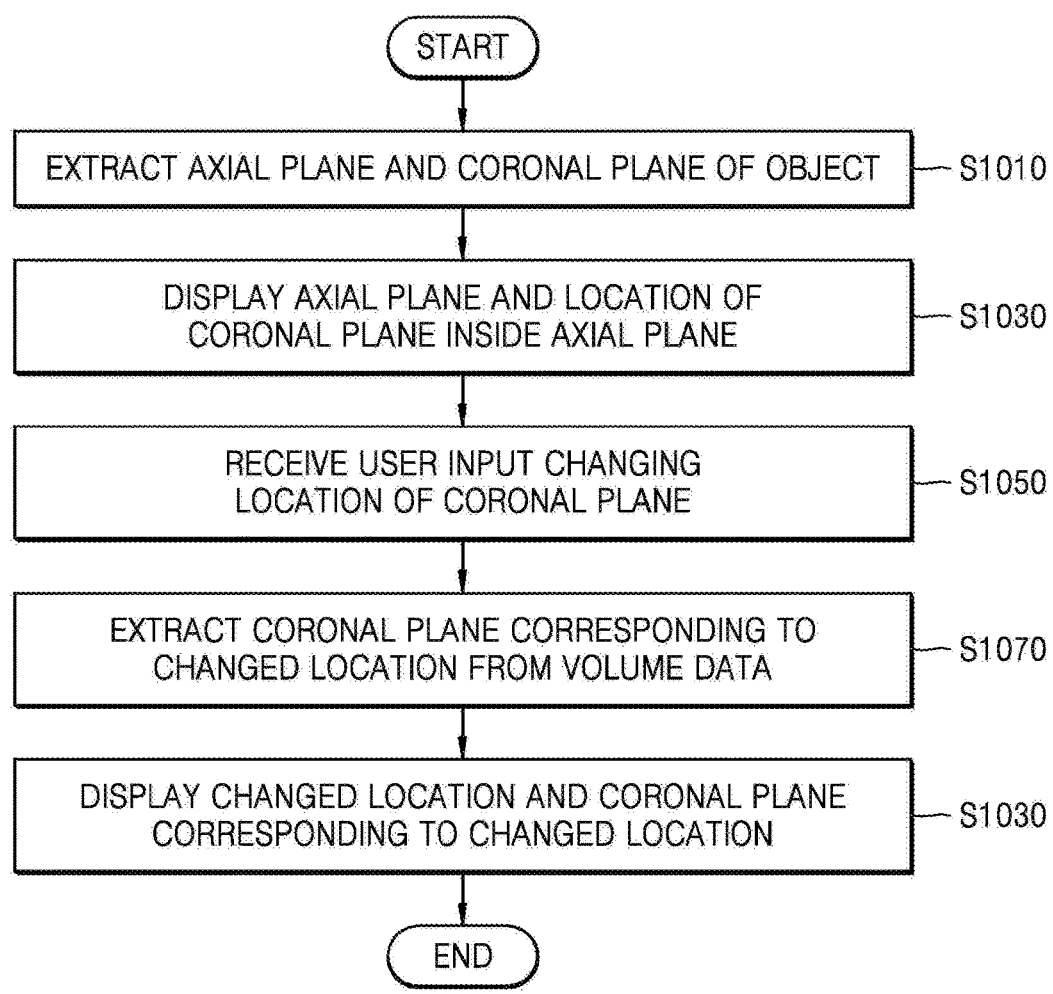
FIG. 10 is a flowchart illustrating a method of operating an ultrasound diagnosis apparatus according to an embodiment.

FIG. 10 is a flowchart illustrating a method of operating an ultrasound diagnosis apparatus according to an embodiment.

The method of operating the ultrasound diagnosis apparatus according to an embodiment may include means for changing a location of an extracted coronal plane. The method of operating the ultrasound diagnosis apparatus according to FIG. 10 may include extracting an axial plane and a coronal plane of an object (S1010), displaying an axial plane and a location of the coronal plane inside the axial plane (S1030), receiving a user input changing a location of the coronal plane (S1050), extracting a coronal plane corresponding to the changed location from volume data (S1070), and displaying the changed location and a coronal plane corresponding to the changed location (S1090). Since descriptions of a specific method are the same as the descriptions of the ultrasound diagnosis apparatus described with reference to FIGS. 3 to 9, descriptions thereof are omitted.

Figure 11:
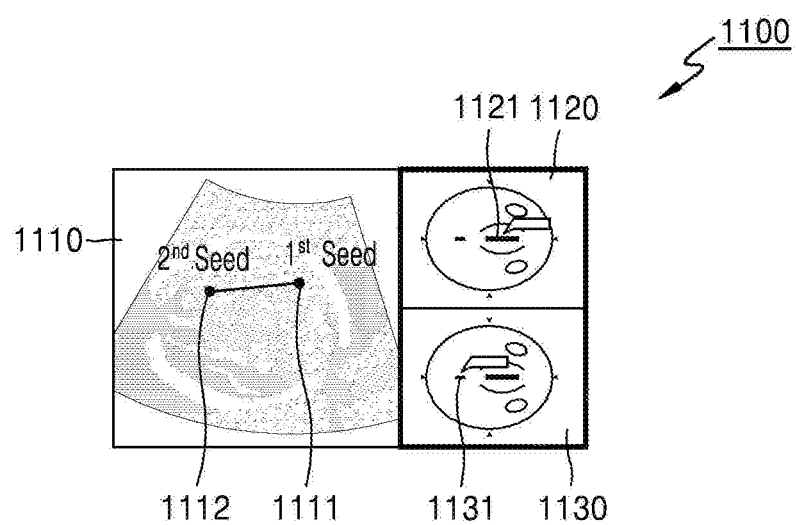
FIG. 11 is a diagram illustrating a screen that receives a user input selecting a reference object in a reference cross-section according to an embodiment.

FIG. 11 is a diagram illustrating a screen that receives a user input selecting a reference object in a reference cross-section according to an embodiment.

An ultrasound diagnosis apparatus according to an embodiment may extract an arbitrary reference cross-section 1110 from initial volume data and display the extracted cross-section 1110 in order to normalize volume data of an object. The arbitrary reference cross-section may be one of axial planes, that is, a TV, a TT, and a TC. For example, the display 370 may display a reference cross-section of an object extracted from volume data, and display a reference object selection window 1120 (1130) in which a location of a reference object is selected by a user. A user may select and input points 1121 and 1131 considered to correspond to a location of each reference object via the reference object selection window 1120 (1130). When the ultrasound diagnosis apparatus receives an input of the points 1121 and 1131 from a user, reference objects 1111 and 1112 may be displayed at locations corresponding to the input points 1121 and 1131 on the reference cross-section 1110 in the display screen. After that, the image processor 350 of the ultrasound diagnosis apparatus may normalize volume data of an object by using location information of the reference object.

Figure 12:
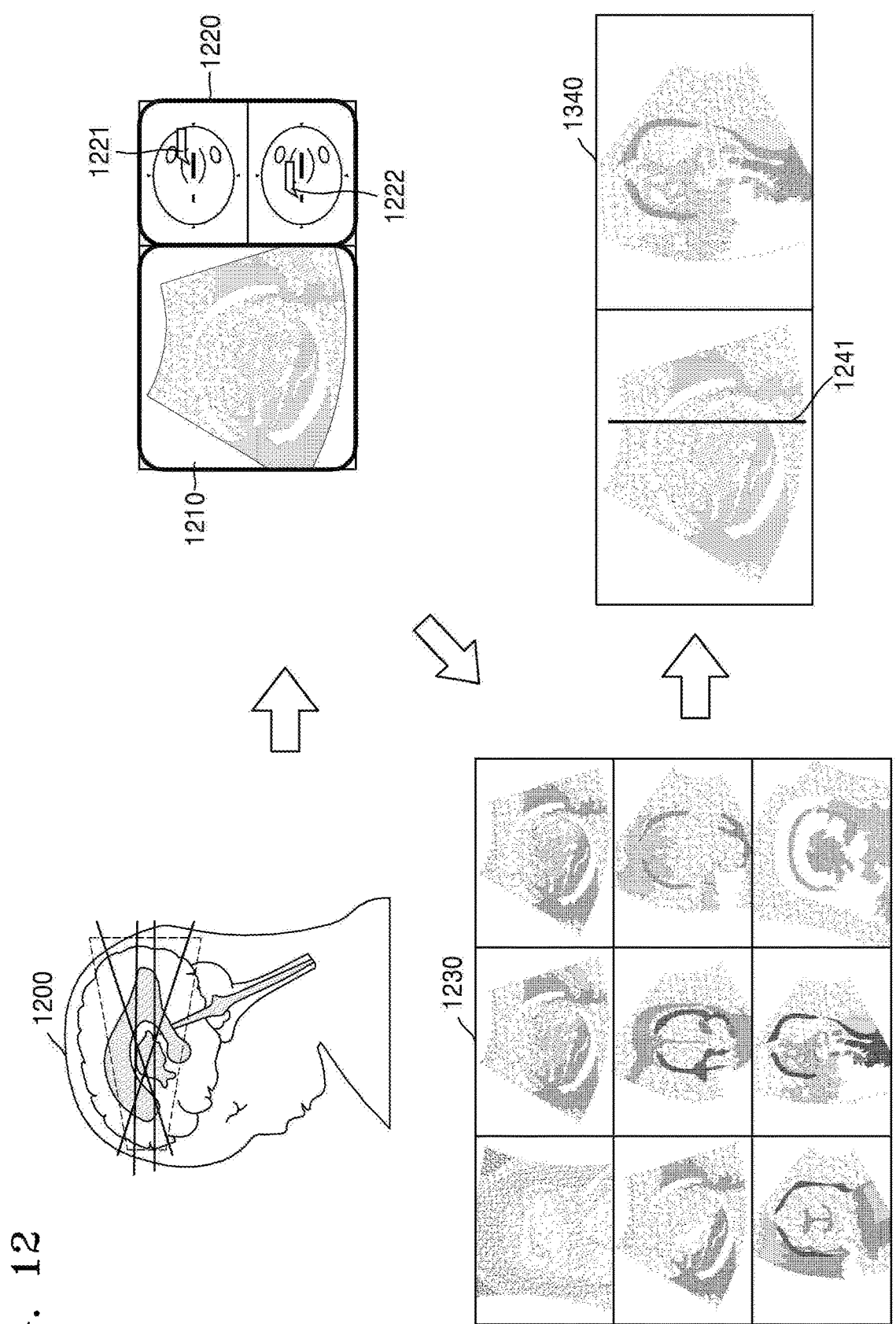
FIG. 12 is a diagram illustrating an operation screen according to an embodiment.

FIG. 12 is a diagram illustrating an operation screen according to an embodiment.

The ultrasound diagnosis apparatus according to an embodiment may obtain initial volume data of an object 1200 via the data obtainer 330. The display 370 may extract an arbitrary reference cross-section from the initial volume data and display (1210) the extracted cross-section, and simultaneously display a window 1220 for receiving location information of a reference object from a user. The ultrasound diagnosis apparatus may normalize the volume data based on location information 1221 and 1222 of the reference object received from the user. After that, the image processor 350 may automatically extract a coronal plane of an object based on information of at least one anatomical landmark included in the normalized volume data. In this case, the image processor 350 may automatically extract and display an axial plane and a sagittal plane together as well as the coronal plane. A user may diagnose and observe a state of the object accurately and swiftly in views of various angles via a displayed entire result screen 1230. In the case where a location of a standard cross-section extracted from the object should be changed, an edit screen 1240 for changing the location of the cross-section may be displayed. The edit screen 1240 may display the standard cross-section (for example, one of coronal planes) which the user desires to edit and an arbitrary reference cross-section (for example, one of axial planes) for representing a relative location of the standard cross-section. The user may move an indicator 1241 on the reference cross-section and obtain a changed standard cross-section corresponding to a location of the changed indicator 1241 in real-time. Therefore, the user may directly edit the standard cross-section automatically extracted from the ultrasound diagnosis apparatus.

While one or more embodiments have been described with reference to the figures, it will be understood by those of ordinary skill in the art that various changes in form and details may be made therein without departing from the spirit and scope as defined by the following claims.

What is claimed is:

1. An ultrasound diagnosis apparatus comprising:
a memory configured to store data;
a display configured to display a reference cross-section of a target object extracted from volume data of the target object;
a user input unit configured to receive a user selection input selecting a reference object included in the reference cross-section; and
an image processor configured to normalize the volume data by using location information of the reference object, detect at least one anatomical landmark in the normalized volume data based on a predetermined reference value stored in the memory, and extract a coronal plane of the target object from the normalized volume data, so that the coronal plane comprises the at least one anatomical landmark detected based on the predetermined reference value comprising information of at least one from among a kind, a location, a brightness, and a shape, of the at least one anatomical landmark,
wherein the display is further configured to display the coronal plane,
the at least one anatomical landmark comprises an anatomical portion of the target object that allows standard cross-sections of the target object to be identified, and
the coronal plane is one of the standard cross-sections.

2. The ultrasound diagnosis apparatus of claim 1, wherein the at least one anatomical landmark comprises at least one from among a cavum septum pellucidum (CSP), thalami, a cerebellum, a ventricle, a choroid plexus (CP), a sphenoid bone, a caudate nucleus, and an inter-hemispheric fissure (IHF).

3. The ultrasound diagnosis apparatus of claim 1, wherein the target object comprises a human body or a brain of a fetus.

4. The ultrasound diagnosis apparatus of claim 1, wherein the image processor is further configured to extract at least one from among an axial plane and a sagittal plane of the target object from the normalized volume data,
the display is further configured to display the at least one from among the axial plane and the sagittal plane, and
the axial plane and the sagittal plane are included in the standard cross-sections of the target object.

5. The ultrasound diagnosis apparatus of claim 4, wherein the axial plane comprises at least one from among a trans-ventricular axial plane (TV), a trans-thalamic axial plane (TT), and a trans-cerebellar axial plane (TC),
the sagittal plane comprises at least one from among a mid-sagittal plane (MPS) and a para-sagittal plane (PSP), and
the coronal plane comprises at least one from among a trans-frontal coronal plane (TFc), a trans-caudate coronal plane (TCaudc), a trans-thalamic coronal plane (TTc), and a trans-cerebellar coronal plane (TCc).

6. The ultrasound diagnosis apparatus of claim 1, wherein the image processor is further configured to extract an axial plane of the target object that is one of the standard cross-sections of the target object,
the display is further configured to display the axial plane and a location of the coronal plane inside the axial plane,
the user input unit is further configured to receive a user input that changes the location of the coronal plane, and
the image processor is further configured to extract another coronal plane corresponding to the changed location, from the normalized volume data.

7. The ultrasound diagnosis apparatus of claim 6, wherein the display is further configured to display the changed location on the axial plane and the another coronal plane corresponding to the changed location.

8. The ultrasound diagnosis apparatus of claim 6, wherein the image processor is further configured to calculate a difference between the location of the coronal plane before the change of location and a location of the another coronal plane after the change of location, and
the display is further configured to display the another coronal plane corresponding to the changed location and the difference.

9. A method of operating an ultrasound diagnosis apparatus, the method comprising:
displaying a reference cross-section of a target object extracted from volume data of the target object;
receiving a user selection input selecting a reference object included in the reference cross-section;
normalizing the volume data by using location information of the reference object;
detecting at least one anatomical landmark in the normalized volume data based on a predetermined reference value stored in a memory of the ultrasound diagnosis apparatus; and
extracting a coronal plane of the target object from the normalized volume data, so that the coronal plane comprises the at least one anatomical landmark detected based on the predetermined reference value comprising information of at least one from among a kind, a location, a brightness, and a shape, of the at least one anatomical landmark; and
displaying the coronal plane,
wherein the at least one anatomical landmark comprises an anatomical portion of the target object that allows standard cross-sections of the target object to be identified, and
the coronal plane is one of the standard cross-sections.

10. The method of claim 9, wherein the at least one anatomical landmark comprises at least one from among a cavum septum pellucidum (CSP), thalami, a cerebellum, ventricle, a choroid plexus (CP), a sphenoid bone, a caudate nucleus, and an inter-hemispheric fissure (IHF).

11. The method of claim 9, wherein the target object comprises a human body or a brain of a fetus.

12. The method of claim 9, further comprising:
extracting at least one from among an axial plane and a sagittal plane of the target object from the normalized volume data; and
displaying the at least one from among the axial plane and the sagittal plane,
wherein the axial plane and the sagittal plane are included in the standard cross-sections of the target object.

13. The method of claim 12, wherein the axial plane comprises at least one from among a trans-ventricular axial plane (TV), a trans-thalamic axial plane (TT) and a trans-cerebellar axial plane (TC),
the sagittal plane comprises at least one from among a mid-sagittal plane (MPS) and a para-sagittal plane (PSP), and
the coronal plane comprises at least one from among a trans-frontal coronal plane (TFc), a trans-caudate coronal plane (TCaudc), a trans-thalamic coronal plane (TTc), and a trans-cerebellar coronal plane (TCc).

14. The method of claim 9, further comprising:
extracting an axial plane of the target object, the axial plane being one of the standard cross-sections of the target object;
displaying the axial plane and a location of the coronal plane inside the axial plane;
receiving a user input that changes the location of the coronal plane; and
extracting another coronal plane corresponding to the changed location from the normalized volume data.

15. The method of claim 14, further comprising:
displaying the changed location on the axial plane and the another coronal plane corresponding to the changed location.

16. The method of claim 14, further comprising:
calculating a difference between the location of the coronal plane before the change of location and a location of the another coronal plane after the change of location; and
displaying the another coronal plane corresponding to the changed location and the difference.

\* \* \* \* \*